United States Patent [19]

Vecchietti et al.

[11] Patent Number: 4,507,307

[45] Date of Patent: Mar. 26, 1985

[54] N$_1$-ACYL-3-AMINO-1,2,3,4-TETRAHYDROQUINOLINE COMPOUNDS ACTIVE ON THE CARDIOCIRCULATORY SYSTEM

[75] Inventors: Vittorio Vecchietti; Emilio Mussini; Giorgio Ferrari, all of Milan, Italy

[73] Assignee: Simes, Milan, Italy

[21] Appl. No.: 402,551

[22] Filed: Jul. 28, 1982

[30] Foreign Application Priority Data

Jul. 29, 1981 [IT] Italy ................ 23213 A/81

[51] Int. Cl.$^3$ ............... A61K 31/47; C07D 215/38
[52] U.S. Cl. .................... 514/313; 546/159; 514/314
[58] Field of Search .............. 424/258; 546/159

[56] References Cited

U.S. PATENT DOCUMENTS

| | | |
|---|---|---|
| 2,554,737 | 5/1951 | Haefliger et al. ............ 546/159 |
| 2,942,024 | 6/1960 | Baker ............................ 562/401 X |
| 3,362,959 | 1/1968 | Cocker et al. ................ 562/401 X |
| 3,389,140 | 6/1968 | Montzka ...................... 562/401 X |
| 3,389,141 | 6/1968 | Montzka ...................... 562/401 X |
| 3,452,026 | 6/1969 | Perron et al. ................. 424/258 X |
| 3,798,226 | 3/1974 | Meguro et al. .............. 424/258 X |
| 4,215,223 | 7/1980 | Kessels ......................... 562/401 |

FOREIGN PATENT DOCUMENTS 0013741  8/1966  Japan .................................. 546/159

OTHER PUBLICATIONS

Kusuda et al., Chemical Abstracts, vol. 62, 1632a–c, (1965).
Kusuda et al., Chemical Abstracts, vol. 65, No. 13, Dec. 19, 1966, abstract No. 20107g.
Columbus Ohio, (U.S.) and JP—A—13741/66, (Nippon Shinyaku).

*Primary Examiner*—Donald G. Daus
*Assistant Examiner*—Diana G. Rivers
*Attorney, Agent, or Firm*—Stevens, Davis, Miller & Mosher

[57] ABSTRACT

N$_1$-acyl-3-amino-1,2,3,4-tetrahydroquinoline compounds active on the cardiocirculatory system, pharmaceutically acceptable salts thereof, pharmaceutical compositions containing the new compounds and some intermediates useful in the preparation of the new tetrahydroquinoline compounds.

Process for preparing the new tetrahydroquinoline compounds and some intermediates useful in the preparation thereof.

14 Claims, No Drawings

$N_1$-ACYL-3-AMINO-1,2,3,4-TETRAHYDROQUINOLINE COMPOUNDS ACTIVE ON THE CARDIOCIRCULATORY SYSTEM

This invention relates to new tetrahydroquinoline compounds active on the cardiocirculatory system, pharmaceutically acceptable salts thereof, pharmaceutical compositions containing them and some intermediates useful in the preparation of the new tetrahydroquinoline compounds.

It is a further object of this invention to provide a process for preparing the new tetrahydroquinoline compounds and some intermediates useful in the preparation thereof.

More particularly the new tetrahydroquinoline compounds of this invention have the following general formula:

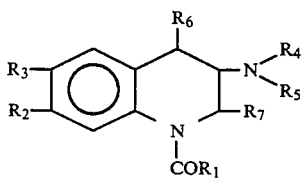

wherein $R_1$ is selected from the group comprising a straight or branched chain alkyl having from 1 to 20 carbon atoms, cycloalkyl having from 3 to 6 carbon atoms, aryl, substituted aryl, aralkyl, substituted aralkyl, heterocycle and substituted heterocycles, $R_2$ and $R_3$ are the same or different and each is selected from the group comprising hydrogen atom, hydroxyl and alkoxyl having from 1 to 6 carbon atoms, provided that at least one of them is different from hydrogen, $R_4$, $R_5$, $R_6$ and $R_7$ are the same or different and each is selected from the group comprising hydrogen atom and alkyl having from 1 to 6 carbon atoms.

The compounds having formula (I) may be prepared by $N_1$-acylation of the compounds of the formula:

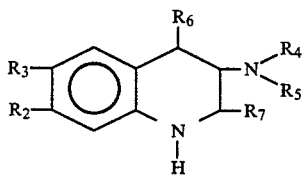

wherein $R_2$, $R_3$, $R_4$, $R_5$, $R_6$ and $R_7$ have the meanings stated above. The 1,2,3,4-tetrahydroquinolines of the formula (II) are new and are a further object of the present invention.

The 1,2,3,4-tetrahydroquinolines of the formula (II) are prepared by reducing the 3-aminoquinolines of the formula:

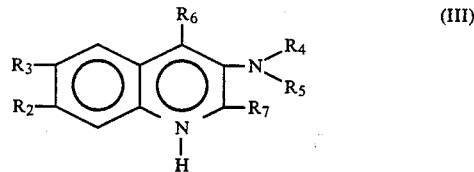

wherein $R_2$, $R_3$, $R_4$, $R_5$, $R_6$ and $R_7$ have the above mentioned meanings.

The compounds of the formula (III) are prepared according to commonly used techniques; the compounds of the formula (III), in which $R_4$ and/or $R_5$ are alkyl radicals, may be prepared by alkylation of the amino group in the 3-position of the corresponding 3-aminoquinolines.

The 1,2,3,4-tetrahydroquinolines having formula (II) are $N_1$ acylated with an acid of the formula $R_1COOH$, wherein $R_1$ has the above mentioned meanings, or with an reactive derivative thereof such as a halide or an anhydride. When the derivative is a halide, the reaction is carried out in the presence of an aprotic solvent, such as methylene chloride, chloroform, benzene, toluene, dioxane, acetone, tetrahydrofurane, etc., at a temperature between $-20°$ C. and the boiling temperature of the reaction mixture; preferably in the presence of a hydrogen halide binding agent such as tertiary organic bases selected from the group comprising pyridine, triethylamine, diisopropylethyleneamine or inorganic bases selected from the group comprising sodium and potassium carbonate, sodium and potassium bicarbonate, or organic oxides selected from the group comprising ethylene oxide, propylene oxide, butylene oxide, etc.

When the reactive derivative is an anhydride the reaction is preferably carried out at a temperature between room temperature and the boiling temperature of the reaction mixture. The reaction may be carried out in the presence of an excess of the anhydride or, preferably, in an aprotic solvent such as benzene, toluene, xylene, tetrahydrofurane, dioxane, etc.

The reactive derivative may be also a mixed anhydride such as the mixed anhydrides of an acid of the formula $R_1COOH$ with (a) carbonic acid derivatives, for instance isobutylchloroformate and ethylchloroformate, or (b) phosphoric acid derivatives, for instance diphenylchlorophosphate. In this case the reaction is preferably carried out in an aprotic solvent such as tetrahydrofurane, dioxane, toluene, xylene, at a temperature between $-30°$ C. and $+30°$ C.

When $R_4$ and/or $R_5$ in formula (II) are hydrogen atoms, it is necessary to avoid the acylation of the amino group in the 3-position.

This primary amino group may be protected, for example, by forming a Schiff base, with a protecting group which may be easily removed, after the acylation step, by adding water and an acid, such as dilute hydrochloric acid, dilute sulforic acid, oxalic acid.

The thus obtained compounds of the formula (I), in which $R_4$ and $R_5$ are hydrogen atoms, may be then alkylated to give the corresponding monoalkyl or dialkyl derivatives ($R_4$ and/or $R_5$=alkyl) by conventional means, for example by reaction with an alkyl halide in the presence of a base. The amino group may also be alkylated by reaction with a carbonyl compound, such as an aldehyde or a ketone, and by subsequent reduction with a suitable reducing agent, for example formic acid, hydrogen catalysts, sodium borohydride, etc.

The monoalkyl derivatives may also be obtained by dealkylation of compounds of formula (I) in which both $R_4$ and $R_5$ are alkyl radicals.

This dealkylation step may be carried out by treating the compound of the formula (I), in which both $R_4$ and $R_5$ are alkyl radicals, with a carbonic acid derivative, such as trichloroethylchloroformate; the thus obtained urethane affords the corresponding monoalkyl derivative by means of a mild reductive saponification.

Preferably, this reaction is carried out by heating the reactants at the boiling temperature of the solvent, which may be an aprotic solvent such as an aromatic hydrocarbon or a chlorinated solvent; optionally in the presence of an inorganic base, such as sodium or potassium carbonate or sodium or potassium bicarbonate; the saponification step is preferably carried out with zinc and acetic acid, at a temperature between 10° C. and 50° C.

The 1,2,3,4-tetrahydroquinolines of the formula (II) may be prepared by reducing the corresponding quinolines of the formula (III) with hydrogen in the presence of a catalyst such as platinum or palladium on charcoal, Raney nickel, rhodium on alumina, etc.; this step is carried out under pressure, preferably between 4 and 150 bar, at a temperature between room temperature and 150° C. and in the presence of a suitable solvent such as acetic acid, methanol, ethanol, xylene, toluene, dioxane, tetrahydrofurane, indane, 1,2,3,4-tetrahydronaphthalene, decahydronaphthalene. The quinolines of the formula (III) may be prepared according to the commonly used techniques; when $R_4$ and/or $R_5$ are alkyl radicals, the quinolines embraced by formula (III) may be prepared from the corresponding 3-aminoquinolines via alkylation of the amino group according to the above indicated procedure, for example by reacting them with a carbonyl compound or by dissolving them into an acid of the formula $R_8COOH$ or $R_9COOH$ (wherein $R_8$ and $R_9$ correspond to the alkyl radicals $R_4$ and $R_5$ less a methylene group) and adding a suitable reducing agent such as sodium borohydride.

A monoalkylated 3-amino-1,2,3,4-tetrahydroquinoline is thus obtained. In order to introduce a further alkyl radical, the above described procedure may be repeated.

Alternatively the alkylation may be carried out by preparing the amide corresponding to the desired amine and by reducing it with a suitable reducing agent, such as lithium aluminum hydride, diborane, etc. Even in this case a monoalkylamine is obtained. This procedure may be repeated in order to obtain the dialkylated compound.

The 1,2,3,4-tetrahydroquinolines of general formulae I and II contain from 1 to 3 asymmetric atoms; one of these is the carbon atom in the 3-position; when $R_6$ and/or $R_7$ are not hydrogen the carbon atoms in the position 4 and/or 2 are asymmetric too. The present invention is intended to cover either the single stereoisomers or the mixtures thereof.

When the compound contains more than one asymmetric atom there will be obtained a mixture of diastereoisomers which, in turn, consist of a couple of enantiomers; each of the two enantiomers can be separated from the mixture by means of the commonly used resolving agents, such as (+) or (−) camphosulfonic acid, (+) or (−) tartaric acid, (+) or (−) O,O-diacyltartaric acid, (+) or (−) glutamic acid, (+) or (−) malic acid, (+) or (−) tartronylic acids.

The separation of the stereoisomers may be carried out either on the final products or on the intermediates of the formula II.

A further object of the present invention are the salts of the compounds of the formula I with pharmaceutically acceptable organic or inorganic acids such as hydrochloric acid, hydrobromic acid, sulfonic acid, phosphonic acid, methane sulfonic acid, arylsulfonic acid, maleic acid, fumaric acid, citric acid or tartaric acid.

Because of their activity on the cardiocirculatory system, the compounds of the present invention are particularly useful as cardiotonics.

The activity on the cardiocirculatory system has been demonstrated by means of standard pharmacological tests both in vitro and in vivo.

In vitro it has been proved that the solutions of products of the formula (I) (concentration $3 \cdot 10^{-4}M$) increase the contraction force of the papillary muscle of the cat (Cattel and Gold: J. Pharmacol. Exp. Ther., 62, 116, 1938).

More particularly, the (±)-1-propionyl-3-dimethylamino-6,7-dimethoxy-1,2,3,4-tetrahydroquinoline hydrobromide increases the contraction force of a rate of 85% in comparison with the base line; the (±)-1-isobutyryl-3-dimethylamino-6,7-dimethoxy-1,2,3,4-tetrahydroquinoline hydrochloride of 70%; the (−)-1-isobutyryl-3-dimethylamino-6,7-dimethoxy-1,2,3,4-tetrahydroquinoline of 110%; the (+)-1-isobutyryl-3-dimethylamino-6,7-dimethoxy-1,2,3,4-tetrahydroquinoline of 16,5%; the (±)-1-cyclopropyl-3-dimethylamino-6,7-dimethoxy-1,2,3,4-tetrahydroquinoline hydrochloride of 51%; the (±)-1-pivaloyl-3-dimethylamino-6,7-dimethoxy-1,2,3,4-tetrahydroquinoline hydrochloride of 43%.

Other tests have been carried out in vivo on anaesthetized dogs to which different doses of (±)-1-propionyl-3-dimethylamino-6,7-dimethoxy-1,2,3,4-tetrahydroquinoline and of (±)-1-isobutyryl-3-dimethylamino-6,7-dimethoxy-1,2,3,4-tetrahydroquinoline have been administered by intravenous route (60, 120, 240 µg/kg/min.) or by intraperitoneal route (3, 6 and 12 mg/kg/min.). Both products improve the heart performance by exercising a positive inotropic activity without increasing the cardiac rhythm or increasing it only moderately.

The 1-isobutyryl-3-dimethylamino-6,7-dimethoxy-1,2,3,4-tetrahydroquinoline does not change significantly the systemic resistance, which tends to decrease, and the oxygen amount requested by the cardiac muscle, which increases slightly.

$ED_{50}$ has been measured in vivo in dogs by means of the test of the increase of the heart contraction force; the following results have been obtained: 2.4 mg/kg/i.v. and 12 mg/kg/os.

Moreover, the products of the formula (I) are endowed with low toxicity; for instance, (±)-1-isobutyryl-3-dimethylamino-6,7-dimethoxy-1,2,3,4,-tetrahydroquinoline $DL_{50}$ in mice is 500 mg/kg/os and 70 mg/kg/i.v.; $DL_{50}$ of the levo and dextro isomers thereof is 66 and 93.5 mg/kg/i.v. respectively. This product is even less toxic in dogs; no toxic phenomenon occurs at doses higher than 400 mg/kg/i.v.

Preliminary tests in man have confirmed the favourable properties of the products of the formula (I).

The present invention provides also pharmaceutical compositions containing compounds of the formula (I)

or pharmaceutically acceptable salts thereof as active ingredients.

These compositions may contain the active ingredient together with organic or inorganic, solid or liquid pharmaceutical excipients, suitable for oral, parenteral or rectal administration.

The pharmaceutical compositions may be in solid form, such as tablets, pellets, capsules, powder, granules, or in liquid form as solutions, suspension or emulsions.

The pharmaceutical compositions may be suitable for slow release of the pharmaceutical product after the administration.

The pharmaceutical compositions may contain, together with the excipients, preserving, stabilizing, wetting or emulsifying agents, salt for regulating the osmotic pressure, buffers, dyesfuffs and flavouring agents. They may be prepared according to known methods and may further contain other therapeutic ingredients.

In the following examples all the products obtained in the various steps of the preparation processes of the products of the formula (I) have been characterized; they have been therefore always isolated and purified, but the intermediate products can often be used in the subsequent steps of the process without any previous separation or purification.

All of the given yields have been calculate on the theoretical. The following examples are given to illustrate the present invention, without limiting it in any way.

EXAMPLE 1

3-dimethylamino-6,7-dimethoxyquinoline

A mixture of 113.5 g (2.45 mole) of 99% formic acid and 200 ml of formaldehyde (36.5% w/v) is added, under stirring and by cooling at 15°–20° C., to a solution of 100 g (0.49 mole) of 3-amino-6,7-dimethoxyquinoline (prepared according to J. Med. Chem., 22, 1005, 1979) in 400 ml of N,N-dimethylformamide. The thus obtained mixture is refluxed for 6 hours, then water is added, the pH is adjusted to 10 with 40% NaOH and the mixture is extracted with ethyl acetate.

The organic layer is washed with water, dried over $Na_2SO_4$, concentrated to dryness and the solid residue is crystallized from a mixture of ethyl acetate/benzine ½, 108 g of 3-dimethylamino-6,7-dimethoxyquinoline are obtained; m.p. 118°–120° C.

Yield: 95%.

By analogous procedures and by using the suitably substituted 3-amino-quinolines the following compounds have been prepared:

3-dimethylamino-6-methoxy-quinoline monohydrochloride, m.p. 233°–235° C. (EtOH), yield 80%.

3-dimethylamino-7-methoxy-quinoline dihydrochloride, m.p. 210°–220° C. (EtOH), yield 85%.

EXAMPLE 2

(±)3-dimethylamino-6,7-dimethoxy-1,2,3,4-tetrahydroquinoline dihydrochloride 30 g (0.129 mole) of 3-dimethylamino-6,7-dimethoxyquinoline, prepared according to example 1, in 200 ml of acetic acid are hydrogenated in a Parr apparatus in the presence of 3 g of palladium on 10% charcoal, at 4 bar and at 80° C.

When the hydrogen absorption is completed, the catalyst is filtered and the reaction mixture is concentrated to dryness.

The oily residue is dissolved in water, neutralized with solid $NaHCO_3$ and washed twice with ethyl acetate which is discharged; the pH of the aqueous layer is adjusted to 10 with 40% NaOH and the mixture is extracted with $CHCl_3$.

The chloroform layer is concentrated to dryness and then treated with alcoholic HCl to give a crystalline solid which is filtered and crystallized from anhydrous ethyl alcohol, to afford 20 g of (±)3-dimethylamino-6,7-dimethoxy-1,2,3,4-tetrahydroquinoline dihydrochloride; yield 50%; m.p. 213°–215° C. (EtOH) (monohydrochloride m.p. 177°–180° C., EtOH).

By analogous procedures the following compounds have been prepared:

(±)3-dimethylamino-6,7-methylenedioxy-1,2,3,4-tetrahydroquinoline dihydrochloride, m.p. 161°–164° C. (EtOH), yield 40%.

(±)3-dimethylamino-6-methoxy-1,2,3,4-tetrahydroquinoline dihydrochloride, m.p. 198°–202° C. (EtOH), yield 45%.

(±)3-dimethylamino-7-methoxy-1,2,3,4-tetrahydroquinoline dihydrochloride, m.p. 205°–210° C. (EtOH), yield 45%.

(±)3-amino-6,7-dimethoxy-1,2,3,4-tetrahydroquinoline dihydrochloride, m.p. 215°–218° C. (EtOH), yield 25%.

(±)3-amino-6,7-methylenedioxy-1,2,3,4-tetrahydroquinoline, yield 40%.

(±)3-amino-6-methoxy-1,2,3,4-tetrahydroquinoline dihydrochloride, m.p. 234°–238° C. (EtOH), yield 50%.

(±)3-amino-7-methoxy-1,2,3,4-tetrahydroquinoline dihydrochloride, m.p. 215°–218° C. (EtOH), yield 25%

EXAMPLE 3

Resolution of the (±)3-dimethylamino-6,7-dimethoxy-1,2,3,4-tetrahydroquinoline 28 g (0.112 mole) of d(±)camphosulfonic acid monohydrate are added to a solution of 13 g (0.056 mole) of 3-dimethylamino-6,7-dimethoxy-1,2,3,4-tetrahydroquinoline base in 90 ml of acetone.

The mixture is heated untill the dissolution is completed and then is allowed to cool to room temperature. The crystallized solid is filtered and washed with cold acetone to give 15 g of the diastereoisomer salt (A), m.p. 181°–184° C.

$[\alpha]_D^{20}$ +16.7° (c=1% EtOH); yield 38.4%.

The acetonic mother liquors are concentrated to dryness, dissolved in the smallest possible amount of acetone; ether is added to incipient turbidity. Upon standing, 11.7 g (yield 30%) of diastereoisomer salt (B) crystallize; m.p. 153°–155° C.

$[\alpha]_D^{20}$ +42.3° (c=1% EtOH).

From the camphosulfonate (A), the (−)-3-dimethylamino-6,7-dimethoxy-1,2,3,4-tetrahydroquinoline dihydrochloride, m.p. 177°–179° C., $[\alpha]_D^{20}$ −13.2° (c=1% EtOH) and from the diastereoisomer salt (B) the (+)-3-dimethylamino-6,7-dimethoxy-1,2,3,4-tetrahydroquinoline dihydrochloride, m.p. 180°–182° C., $[\alpha]_D^{20}$ +12.6° (c=1% EtOH) are obtained in stochiometric amounts according to the usual techniques.

EXAMPLE 4

N₁-acylation of the products of formula II (A)

0.1 mole of a compound of general formula II and 0.5 mole of a tertiary organic base in 200 ml of methylene chloride are cooled to 0° C. and 0.12 mole of the halide of an acid of general formula R₁COOH are added; the mixture is allowed to stand at room temperature untill the reaction is completed, then it is washed with diluted NaOH and water.

The extracted organic layer, after removal of the solvent and of the tertiary base, affords a residue which can be isolated as base, or transformed into the desired salt according to the usual tecniques.

(B)

0.1 mole of the compound of general formula II and 0.25 mole of an anhydride in 200 ml of anhydrous toluene are kept at 90° C. until the reaction is completed. The toluene solution is washed with diluted NaOH, dried and evaporated to dryness to afford the desired product.

(C)

A solution of 0.15 mole of an acid in 200 ml of anhydrous tetrahydrofurane is cooled to −25° C. and treated with 0.16 mole of triethylamine and 0.15 mole of isobutylchloroformate. After stirring at −25° C. for 15 min. a solution of 0.1 mole of the compound of general formula II in 50 ml of tetrahydrofurane is added. The reaction mixture is stirred at −25° C. for further 30 min., then is heated to 20° C. for 1 hour.

Tetrahydrofurane is evaporated in vacuo at room temperature and the residue is treated with ethyl acetate and water. The organic layer is evaporated to afford the desired product.

By the above indicated procedures the following compounds have been prepared:

(1) (±)-1-acetyl-3-dimethylamino-6,7-dimethoxy-1,2,3,4-tetrahydroquinoline, m.p. 145°–147° C. (EtOAc/benzine), yield 70%

(2) (±)-1-propionyl-3-dimethylamino-6,7-dimethoxy-1,2,3,4-tetrahydroquinoline hydrochloride, m.p. 135°–137° C. (acetone), yield 65%

(3) (±)-1-butyryl-3-dimethylamino-6,7-dimethoxy-1,2,3,4-tetrahydroquinoline hydrobromide, m.p. 127°–130° C. (acetone/ether), yield 60%

(4) (±)-1-isobutyryl-3-dimethylamino-6,7-dimethoxy-1,2,3,4-tetrahydroquinoline hydrochloride, m.p. 216°–219° C. (EtOH), yield 80%

(5) (±)-1-pivaloyl-3-dimethylamino-6,7-dimethoxy-1,2,3,4-tetrahydroquinoline, m.p. 120°–122° C. (ethyl ether/benzine), yield 60%

(6) (±)-1-valeroyl-3-dimethylamino-6,7-dimethoxy-1,2,3,4-tetrahydroquinoline oil, yield 65%

(7) (±)-1-palmitoyl-3-dimethylamino-6,7-dimethoxy-1,2,3,4-tetrahydroquinoline, m.p. 68°–70° C. (ethyl ether/benzine), yield 55%

(8) (±)-1-stearoyl-3-dimethylamino-6,7-dimethoxy-1,2,3,4-tetrahydroquinoline hydrochloride, m.p. 98°–100° C. (acetone), yield 60%

(9) (±)-1-cyclopropylcarbonyl-3-dimethylamino-6,7-dimethoxy-1,2,3,4-tetrahydroquinoline hydrochloride, m.p. 197°–198° C. (EtOH/ether), yield 65%

(10) (±)-1-cyclobutylcarbonyl-3-dimethylamino-6,7-dimethoxy-1,2,3,4-tetrahydroquinoline hydrochloride, m.p. 172°–174° C. (acetone/ether), yield 70%

(11) (±)-1-cyclopentylcarbonyl-3-dimethylamino-6,7-dimethoxy-1,2,3,4-tetrahydroquinoline hydrochloride, m.p. 202°–203° C. (acetone/ether), yield 65%

(12) (±)-1-cyclohexylcarbonyl-3-dimethylamino-6,7-dimethoxy-1,2,3,4-tetrahydroquinoline hydrochloride, m.p. 199°–200° C. (EtOH/ether), yield 70%

(13) (±)-1-benzoyl-3-dimethylamino-6,7-dimethoxy-1,2,3,4-tetrahydroquinoline, m.p. 110°–112° C. (ether/benzine), yield 70%

(14) (±)-1-p-chlorobenzoyl-3-dimethylamino-6,7-dimethoxy-1,2,3,4-tetrahydroquinoline sulfate, m.p. 146°–150° C. (acetone), yield 60%

(15) (±)-1-phenylacetyl-3-dimethylamino-6,7-dimethoxy-1,2,3,4-tetrahydroquinoline maleate, m.p. 113°–114° C. (EtOAc), yield 80%

(16) (±)-1,3-phenylpropionyl-3-dimethylamino-6,7-dimethoxy-1,2,3,4-tetrahydroquinoline maleate, m.p. 127°–129° C. (acetone/ether), yield 80%

(17) (±)-1,4-phenylbutyryl-3-dimethylamino-6,7-dimethoxy-1,2,3,4-tetrahydroquinoline oil, yield 70%

(18) (±)-1-cinnamoyl-3-dimethylamino-6,7-dimethoxy-1,2,3,4-tetrahydroquinoline, m.p. 97°–98° C. (cyclohexane), yield 80%

(19) (±)-1-nicotinoyl-3-dimethylamino-6,7-dimethoxy-1,2,3,4-tetrahydroquinoline sulfate, m.p. 206°–208° C. (EtOH), yield 65%

(20) (±)-1-isonicotinoyl-3-dimethylamino-6,7-dimethoxy-1,2,3,4-tetrahydroquinoline hydrochloride, m.p. 180°–184° C. (EtOH/acetone), yield 60%

(21) (±)-1-picolynoyl-3-dimethylamino-6,7-dimethoxy-1,2,3,4-tetrahydroquinoline maleate, m.p. 148°–150° C. (EtOH), yield 60%

(22) (±)-1,5-dibromo-nicotinoyl-3-dimethylamino-6,7-dimethoxy-1,2,3,4-tetrahydroquinoline hydrochloride, m.p. 138°–141° C. (EtOH/ether), yield 60%

(23) (+)-1-isobutyryl-3-dimethylamino-6,7-dimethoxy-1,2,3,4-tetrahydroquinoline hydrochloride, m.p. 224°–226° C. (EtOH), $[\alpha]_D^{20}$ +2.4° (c=1% EtOH) prepared from (+)-3-dimethylamino-6,7-dimethoxy-1,2,3,4-tetrahydroquinoline, yield 80%

(24) (−)-1-isobutyryl-3-dimethylamino-6,7-dimethoxy-1,2,3,4-tetrahydroquinoline hydrochloride, m.p. 224°–226° C. (EtOH) $[\alpha]_D^{20}$ −3.3° (c=1% EtOH) prepared from (−)-3-dimethylamino-6,7-dimethoxy-1,2,3,4-tetrahydroquinoline, yield 80%

(25) (+)-1-propionyl-3-dimethylamino-6,7-dimethoxy-1,2,3,4-tetrahydroquinoline hydrochloride, m.p. 162°–164° C. (acetone), $[\alpha]_D^{20}$ +8° (c=1% EtOH) prepared from (+)-3-dimethylamino-6,7-dimethoxy-1,2,3,4-tetrahydroquinoline, yield 70%

(26) (−)-1-propionyl-3-dimethylamino-6,7-dimethoxy-1,2,3,4-tetrahydroquinoline hydrochloride, m.p. 162°–164° C. (acetone), $[\alpha]_D^{20}$ −9° (c=1% EtOH) prepared from (−)-3-dimethylamino-6,7-dimethoxy-1,2,3,4-tetrahydroquinoline, yield 70%

EXAMPLE 5

(±)-1-isobutyryl-3-methylamino-6,7-dimethoxy-1,2,3,4-tetrahydroquinoline hydrochloride A mixture of 3.06 g (0.01 mole) of (±)-1-isobutyryl-3-dimethylamino-6,7-dimethoxy-1,2,3,4-tetrahydroquinoline, 15 g (0.15 mole) of potassium bicarbonate and of 6.75 ml (0.05 mole) of trichloroethylchloroformate in 50 ml of chloroform is boiled for 15 hours. The organic layer is washed with 5% HCl and water, then dried over sodium sulfate and concentrated to dryness. The solid residue is crystallized from ether at 60°–80° C. to afford 4.1 g of N-trichloroethylcarbamate, m.p. 83°–85° C., yield 80%.

A solution of 1.5 g of the thus obtained compound in 30 ml of acetic acid is treated with 5 g of Zn powder and stirred for 8 hours at 15° C.

After dilution with 200 ml of water the reaction mixture is filtered and the pH is adjusted to >10 with concentrated NH₄OH. The reaction mixture is extracted three times, each with 50 ml of ethyl acetate; after drying over sodium sulfate, ethyl acetate is evaporated in vacuo. The residue is dissolved in a small amount of acetone and then acidified with ethereal hydrochloric acid to afford crystalline (±)-1-isobutyryl-3-methylamino-6,7-dimethoxy-1,2,3,4-tetrahydroquinoline hydrochloride; m.p. 106°–109° C., yield 80%.

EXAMPLE 6

(±)-1-acetyl-3-dimethylamino-6,7-dihydroxy-1,2,3,4-tetrahydroquinoline hydrochloride 5.56 g (20 mmole) of (±)-1-acetyl-3-dimethylamino-6,7-dimethoxy-1,2,3,4-tetrahydroquinoline, obtained according to example 4 (A), are dissolved in 100 ml of methylene chloride; the solution is cooled to 0° C., saturated with BCl₃ and allowed to stand at room temperature for 24 hours. The solvent and the excess of BCl₃ are evaporated in vacuo and the residue is treated with ethyl alcohol saturated with hydrochloric acid. Upon standing a crystalline precipitate is obtained, which is collected by filtration and then crystallized from a mixture of methanol/water/concentrated hydrochloric acid 80/15/5.

3.6 g of 1-acetyl-3-dimethylamino-6,7-dihydroxy-1,2,3,4-tetrahydroquinoline hydrochloride, m.p. 218°–221° C., are thus obtained; yield 63%.

By analogous procedures the following compounds have been prepared:
1-propionyl-3-dimethylamino-6,7-dihydroxy-1,2,3,4-tetrahydroquinoline hydrochloride
1-isobutyryl-3-dimethylamino-6,7-dihydroxy-1,2,3,4-tetrahydroquinoline hydrochloride.

EXAMPLE 7

1-isobutyryl-3-amino-6,7-dimethoxy-1,2,3,4-tetrahydroquinoline

A solution of 3.9 g (26.4 mmole) of p-nitrobenzaldehyde in 20 ml of 99% ethyl alcohol is added to a solution of 5.5 g (26.4 mmole) of 3-amino-6,7-dimethoxy-1,2,3,4-tetrahydroquinoline in 20 ml of ethyl alcohol (99%).

The mixture is kept at 70° C. for 30 min. and then cooled; the crystallized benzylidene derivative is collected by filtration.

7.5 g (22 mmole) of 3-(p-nitrobenzylidene)-amino-6,7-dimethoxy-1,2,3,4-tetrahydroquinoline are thus obtained; yield 84%; m.p. 172°–174° C.

7.5 g (22 mmole) of this product are dissolved in 75 ml of methylene chloride containing 2.8 g of potassium bicarbonate (33 mmoles) and are cooled to 0°–5° C.

2.56 ml (24.2 mmole) of isobutylchloride are dropped under stirring into the thus obtained suspension. The mixture is then allowed to stand for 15 hours at 4° C.; the solvent is evaporated and the residue is dissolved in a mixture of 100 ml of tetrahydrofurane and 100 ml of 10% HCl.

The thus obtained solution is stirred for 1 hour at room temperature, diluted with 200 ml of water and washed with ethyl acetate which is discharged; the pH is then adjusted to 8 with sodium bicarbonate.

The solution is extracted with methylene chloride, after evaporation of the solvent a residue of 1-isobutyryl-3-amino-6,7-dimethoxy-1,2,3,4-tetrahydroquinoline base is obtained. The residue is dissolved in 99% ethyl alcohol; the thus obtained solution is acidified with an alcoholic solution of oxalic acid. Upon standing the oxalate crystallizes; yield 5 g (70%); m.p. 148°–151° C.

What we claim is:

1. A compound of the formula

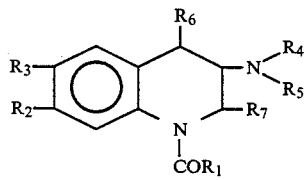

wherein
$R_1$ is selected from the group consisting of a straight or branched chain alkyl having from 1 to 20 carbon atoms, cycloalkyl having from 3 to 6 carbon atoms, phenyl, phenyl substituted by a halogen atom, phenyl alkyl (1–4 C), cinnamoyl, pyridinyl, and pyridinyl substituted by one or two halogen atoms;
$R_2$ and $R_3$ are the same or different and each is selected from the group consisting of a hydrogen atom, hydroxy and alkoxy having from 1 to 6 carbon atoms, provided that at least one of $R_2$ and $R_3$ is different from hydrogen; and
$R_4$, $R_5$, $R_6$ and $R_7$ are the same or different and each is selected from the group consisting of a hydrogen atom and alkyl having from 1 to 6 carbon atoms;
or a pharmaceutically acceptable acid addition salt thereof, said compound being useful in the therapy of affections of the cardiocirculatory system.

2. (±)-1-propionyl-3-dimethylamino-6,7-dimethoxy-1,2,3,4-tetrahydroquinoline useful in the therapy of affections of the cardio-circulatory system, and pharmaceutically acceptable acid addition salts thereof.

3. (+)-1-propionyl-3-dimethylamino-6,7-dimethoxy-1,2,3,4-tetrahydroquinoline useful in the therapy of affections of the cardio-circulatory system, and pharmaceutically acceptable acid addition salts thereof.

4. (−)-1-propionyl-3-dimethylamino-6,7-dimethoxy-1,2,3,4-tetrahydroquinoline useful in the therapy of affections of the cardio-circulatory system, and pharmaceutically acceptable acid addition salts thereof.

5. (±)-1-butyryl-3-dimethylamino-6,7-dimethoxy-1,2,3,4-tetrahydroquinoline useful in the therapy of affections of the cardio-circulatory system, and pharmaceutically acceptable acid addition salts thereof.

6. (+)-1-isobutyryl-3-dimethylamino-6,7-dimethoxy-1,2,3,4-tetrahydroquinoline useful in the therapy of affections of the cardio-circulatory system, and pharmaceutically acceptable acid addition salts thereof.

7. (−)-1-isobutyryl-3-dimethylamino-6,7-dimethoxy-1,2,3,4-tetrahydroquinoline useful in the therapy of affections of the cardio-circulatory system, and pharmaceutically acceptable acid addition salts thereof.

8. (±)-1-pivaloyl-3-dimethylamino-6,7-dimethoxy-1,2,3,4-tetrahydroquinoline useful in the therapy of affections of the cardio-circulatory system, and pharmaceutically acceptable acid addition salts thereof.

9. (±)-1-cyclopropylcarbonyl-3-dimethylamino-6,7-dimethoxy-1,2,3,4-tetrahydroquinoline and pharmaceutically acceptable acid addition salts thereof.

10. A compound of the formula

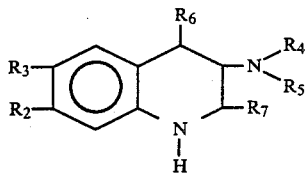

(II)

wherein $R_2$ and $R_3$ are the same or different and each is selected from the group consisting of hydrogen atom, hydroxy and alkoxy having from 1 to 6 carbon atoms, provided that at least one of them is different from hydrogen, $R_4$, $R_5$, $R_6$ and $R_7$ are the same or different and each is selected from the group consisting of hydrogen atom and alkyl having from 1 to 6 carbon atoms, and acid addition salts thereof, said compound being useful in the therapy of affections of the cardio-circulatory system, and pharmaceutically acceptable acid addition salts thereof.

11. A pharmaceutical composition containing an effective amount of a compound of the formula

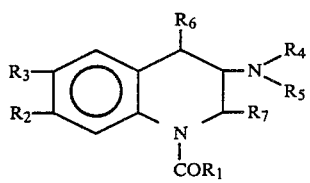

wherein $R_1$ is selected from the group consisting of a straight or branched chain alkyl having from 1 to 20 carbon atoms, cycloalkyl having from 3 to 6 carbon atoms, phenyl, phenyl substituted by a halogen atom, phenyl alkyl (1-4 C), cinnamoyl, pyridinyl, and pyridinyl substituted by one or two halogen atoms;

$R_2$ and $R_3$ are the same or different and each is selected from the group consisting of a hydrogen atom, hydroxy and alkoxy having from 1 to 6 carbon atoms, provided that at least one of $R_2$ and $R_3$ is different from hydrogen; and $R_4$, $R_5$, $R_6$ and $R_7$ are the same or different and each is selected from the group consisting of a hydrogen atom and alkyl having from 1 to 6 carbon atoms; or a pharmaceutically acceptable acid addition salt thereof together with a pharmaceutically acceptable carrier, said compound being useful in the therapy of affections of the cardio-circulatory system.

12. A pharmaceutical composition comprising (±)-1-butyryl-3-dimethylamino-6,7-dimethoxy-1,2,3,4-tetrahydroquinoline or pharmaceutically acceptable salts thereof together with pharmaceutically acceptable carriers, said compositions being useful in the therapy of affections of the cardio-circulatory system.

13. A pharmaceutical composition containing an effective amount of (+)-1-isobutyryl-3-dimethylamino-6,7-dimethoxy-1,2,3,4-tetrahydroquinoline or pharmaceutically acceptable salts thereof together with pharmaceutically acceptable carriers, said compositions being useful in the therapy of affections of the cardio-circulatory system.

14. A pharmaceutical composition containing an effective amount of (−)-1-isobutyryl-3-dimethylamino-6,7-dimethoxy-1,2,3,4-tetrahydroquinoline or pharmaceutically acceptable salts thereof together with pharmaceutically acceptable carriers, said compositions being useful in the therapy of affections of the cardio-circulatory system.

* * * * *